(12) United States Patent
Dhar et al.

(10) Patent No.: US 9,375,426 B2
(45) Date of Patent: Jun. 28, 2016

(54) METHOD OF SCREENING ANTI-PLASMODIAL ACTIVITY OF ACRIFLAVIN AND ACRIFLAVIN AS AN ANTI-MALARIAL AGENT

(71) Applicant: Suman Kumar Dhar, New Dehli (IN)

(72) Inventors: Suman Kumar Dhar, New Dehli (IN); Srikanta Dana, New Dehli (IN); Ashraf Dar, New Dehli (IN); Dhaneswar Prusty, New Dehli (IN); Pritam Mukhopadhyay, New Dehli (IN)

(73) Assignee: Suman Kumar Dhar, New Dehli (IN)

( * ) Notice: Subject to any disclaimer, the term of this patent is extended or adjusted under 35 U.S.C. 154(b) by 0 days.

(21) Appl. No.: 14/423,477

(22) PCT Filed: Jul. 4, 2013

(86) PCT No.: PCT/IN2013/000411
§ 371 (c)(1),
(2) Date: Feb. 24, 2015

(87) PCT Pub. No.: WO2014/030171
PCT Pub. Date: Feb. 27, 2013

(65) Prior Publication Data
US 2015/0216853 A1     Aug. 6, 2015

(30) Foreign Application Priority Data

Aug. 24, 2012 (IN) .......................... 2630/DEL/2012

(51) Int. Cl.
| | |
|---|---|
| *A61K 31/42* | (2006.01) |
| *A61K 31/473* | (2006.01) |
| *G01N 33/569* | (2006.01) |
| *C12Q 1/18* | (2006.01) |
| *C12Q 1/533* | (2006.01) |

(52) U.S. Cl.
CPC ................ *A61K 31/473* (2013.01); *C12Q 1/18* (2013.01); *C12Q 1/533* (2013.01); *G01N 33/56905* (2013.01); *G01N 2333/445* (2013.01); *G01N 2500/02* (2013.01)

(58) Field of Classification Search
CPC ........ A61K 31/473; C12Q 1/533; C12Q 1/18; G01N 33/56905
USPC .......................................................... 514/380
See application file for complete search history.

(56) References Cited

U.S. PATENT DOCUMENTS

2012/0172292 A1    7/2012 Nudler et al.

FOREIGN PATENT DOCUMENTS

WO         0003751       1/2000

OTHER PUBLICATIONS

Weisman et al ,Chemical Biology &Drug Design , Jun. 2006, 67(6), p. 406-409.*

(Continued)

*Primary Examiner* — T. Victor Oh
(74) *Attorney, Agent, or Firm* — Renner Kenner Greive Bobak Taylor Weber

(57) ABSTRACT

The present invention provides a method of screening anti-plasmodial activity of Acriflavin, comprising assessing growth inhibition of *plasmodium* in vitro in chloroquine susceptible and cloroquine resistant *plasmodium* by Acriflavin; or measuring in-vivo *plasmodium* killing ability of Acriflavin; assessing localization of Acriflavin at different stages; and analyzing effect of Acriflavin on gyrase activity wherein said method utilizes Acriflavin in nano-molar range. The present invention relates to potency of Acriflavin (Acriflavin) as an anti-malarial agent both in vitro parasite culture as well as in vivo. More specifically, the invention relates to a method o determining anti-plasmodial activity, Acriflavin as potent anti-malarial agent and also relates to composition(s) comprising Acriflavin.

14 Claims, 4 Drawing Sheets

(56) References Cited

OTHER PUBLICATIONS

Mark Wainwright, 13 pages; Acridine—A neglected antibacterial chromophore; Journal of Antimicrobial Chemotherapy (2001) 47, 1-13.

Jennifer Weisman, et al. 15 pages; Searching for New Antimalarial Therapeutics amongst Known Drugs.

Ramesh Kumar, et al; 7 pages; Acridine: A Versatile Heterocyclic Nucleus.

* cited by examiner

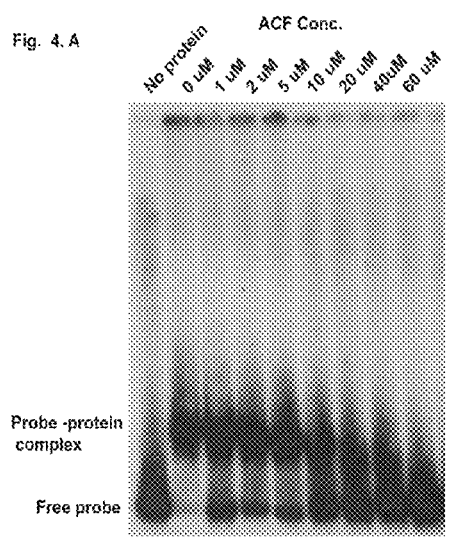
Fig. 4. A
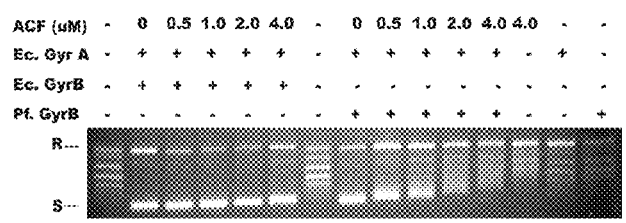
Fig. 4. B
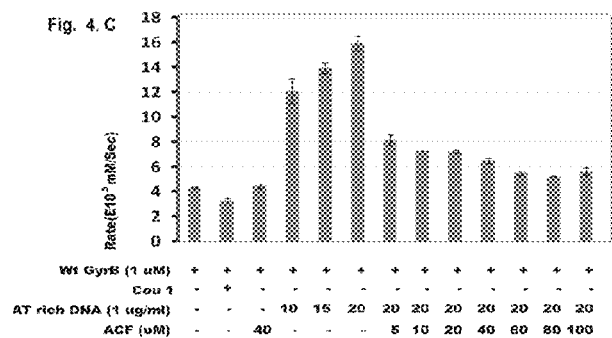
Fig. 4. C

METHOD OF SCREENING ANTI-PLASMODIAL ACTIVITY OF ACRIFLAVIN AND ACRIFLAVIN AS AN ANTI-MALARIAL AGENT

FIELD OF THE INVENTION

The present invention relates to potency of Acriflavin as an anti-malarial agent in both in vitro parasite culture as well as in vivo at a nano molar range. More specifically, the invention relates to a method of determining anti-plasmodial activity of Acriflavin as potent anti-malarial agent at a nano-molar range and composition(s) comprising Acriflavin at a nano molar range.

BACKGROUND OF THE INVENTION

Each year, several hundred million people are infected with *P. falciparum*, which causes the most severe form of malaria in humans leading to 1 to 2 million deaths [Marti M et al., Science. 2004, 306 (5703):1930-3]. The primary chemotherapeutic drugs like Chloroquine and Pyrimethamine are of little use because parasite has developed resistance against them [V. E. Rosario, Nature, 261, 1976, p 585]. Recent reports suggest that resistance to Artemisinin, the only effective anti-malarial drug at present, is now emerging [Dondorp A M et al., N. Engl. J. Med. 361, 455 (2009), Noedl H et al., N. Engl. J. Med. 359, 2619 (2008)]. Therefore, the search for new drugs must continue. In the quest for new drugs, it is also important to revisit the efficacies of some of the drugs whose potential has not been verified in depth for anti-malarial activities. Acriflavin, a mixture of 3,6-diamino-10-methylacridinum chloride (Trypflavin) and 3,6-diaminoacridine (Proflavin) was developed in 1912 by German medical researcher Paul Ehrlich [Wainwright M, J. Antimicrobial Chemothererapy, 2001, 47, 113]. Acriflavin is an anti-bacterial Acridine and it has been used widely as a topical antiseptic (Browning C H et al., Br Med J. 1917, 2 (2951):70-5]. Besides anti-microbial actions, Acriflavin has been recently shown to have potential anti-cancer activity in mice [Lee K et al., Proc Natl Acad Sci USA. 2009; 106 (42):17910-5]. Before the invention of Chloroquine, it was used as anti-malarial. Although Acriflavin had a potential to be used as anti-malarial, the anti-malarial activity of Acriflavin was not studied further in details.

A possible target for antibacterial activity of Acriflavin is DNA topoisomerase/bacterial gyrase. Gyrase is a type II topoisomerase with two subunits (A and B), essential for relieving the positive supercoiling that may arise ahead of replication fork or due to transcription. Gyrase is not only capable of relieving positive supercoiling, it can also introduce negative supercoiling that is the preferred state of bacterial circular chromosome. A mutation in the gyrase B gene (acrB) has been shown to be responsible for making *E. coli* susceptible to Acriflavin (Funatsuki, K et al., JBC, 1997, 272, 13302-08). It was further shown that the DNA binding activity of gyrase enzyme with the acrB mutation was affected in the presence of Acriflavin. These results indicated that gyrase could be a possible target for Acriflavin.

Interestingly, the human malarial parasite *P. falciparum* contains both the subunits of bacterial gyrase essential for the replication and maintenance of apicoplast organelle. Apicoplast has been acquired by the parasites by endosymbiotic pathways thereby making it susceptible to many drugs that target bacterial replication and transcription machinery [Goodman C D, et al., Mol Biochem Parasitol. 2007 April; 152 (2):181-91]. Interestingly, analysis of the gyrase B amino acid sequences from *P. falciparum* and *E. coli* reveal the presence of similar residues around the acrB mutation region. The residue Arg (760) found in acrB mutant *E. coli* strain is identical in PfGyrB Arg (965).

The presence of bacterial type gyrase in *Plasmodium* prompted to investigate the potency of Acriflavin as anti-malarial agent and its mechanism of action. Acriflavin is a FDA approved drug used in clinical trail against cancer with no or minimal toxicity. It is found that Acriflavin not only kills chloroquine sensitive and resistant malaria parasites in vitro in nano molar range, it also suppresses parasite growth significantly in mouse model. Interestingly, it is found that Acriflavin is accumulated specifically in the infected erythrocytes and not in the uninfected erythrocytes. Further, it was found that Acriflavin affects *Plasmodium* gyrase activity in vitro. It remains to be seen further whether gyrase is a target of Acriflavin in vivo too. These findings establish Acriflavin as a potent anti-malarial both in vitro and in vivo that may have far-reaching consequences in the quest of new anti-malarial drugs.

In the present invention, it is shown that Acriflavin is a potent anti-malarial both in vivo and in vitro with IC50 value residing within nanomolar range. Moreover, this inhibition seems mediated through specific accumulation of Acriflavin in the parasites within the infected RBC only. Acriflavin has been known for its trypanocidal, antibacterial and antiviral activities. The effect of Acriflavin on cancer cells has also been reported [Lee K et al., 2009, PNAS, 106 (42):17910-5]. Acriflavin can inhibit the tumor growth in mice possibly through affecting the dimerization of hypoxia inducible factor HIF-1 that plays important role in cancer progression [Lee K et al., 2009, PNAS, 106 (42):17910-5]. These results indeed support the rationale of using Acriflavin in various diseases. Although there is a concern that Acriflavin is a DNA intercalating agent, administration of Acriflavin in patients over five months does not cause any major side effects suggesting the potential use of Acriflavin in clinical trials.

It is found that Acriflavin inhibits *Plasmodium* gyrase activity that is essential for apicoplast DNA replication. It is possible that Acriflavin may have multiple targets. In vitro, acridine derivatives inhibit Topoisomerase II activity and affects hematin formation that may be crucial for haeme detoxification [Auparakkitanon S and Wilairat P., Biochem Biophys Res Commun 2000, 269 (2):406-9; Auparakkitanon S et al. Antimicrob Agents Chemother. 2003, 47 (12):3708-12] Multiple targets lower the possibility of rapid incidence of drug resistance.

The perception and some evidences related to the DNA interacting property of Acridine ring containing compounds go against its widespread use (Lerman L S, PNAS, 1963, Jan. 15; 49: 94-102). In *E. coli*, higher rate of cell death, mutation frequency and blockage of DNA, RNA and protein synthesis takes place following UV exposure of cells in the presence of micromolar level of Acriflavin (1 µg/ml=3.8 µM). [Doudney C. O., Biochem Biophys Res Commun 1964, 15 (1):70-5]. The same study also reports no measurable incidence of mutation in non-UV exposed Acriflavin treated cells. It has been suggested that Acriflavin possibly interacts with UV damage site (thymine dimer, which is otherwise repairable) leading to the increased lethality and mutation rate. These results indicate that Acriflavin may not be mutagenic by itself. However, the exposure to UV light may affect the cells. Since the IC50 value for effective killing of the parasites is within nanomolar range, the concerns over the DNA intercalating and DNA damaging activity of Acriflavin may be over-speculative. The efficient uptake and retention of Acriflavin by the parasites may also add to the potent anti-malarial effect of Acriflavin.

Taken together, it was demonstrated convincingly that Acriflavin shows potent antimalarial activity in both in vitro and in vivo working in the nanomolar range. Moreover, Acriflavin is accumulated specifically in the infected RBC containing parasites and not in the uninfected RBC. Further, it is shown that gyrase is a potential target of Acriflavin in vitro. As per knowledge to date, in vitro and in vivo anti-plasmodial activity of Acriflavin has not been reported so far which makes it a candidate for anti-malarial drug.

OBJECTS OF THE INVENTION

Accordingly, it is an object of the present invention to provide effective agents which exhibit anti-malarial activity.

Another object of the present invention is to provide an agent which exhibits an anti-malarial activity both in vivo and in vitro with IC50 value residing within nanomolar range.

It is also another object of the present invention to show potency of Acriflavin as an anti-malarial agent with target as *Plasmodiun gyrase*

It is still another embodiment of the present invention to provide compositions comprising Acriflavin at nano molar range which is effective as potent anti-malarial agents and drug resistant parasites.

BRIEF DESCRIPTION OF THE DRAWINGS

FIG. 4: Effect of Acriflavin on gyrase activity (A) DNA binding, (B) supercoiling and (C) DNA dependent ATP hydrolysis. (A) Inhibitory effect of Acriflavin on DNA binding. Gel shift assay were performed with wild type PfGyrB (100 nM) protein at the various concentration of Acriflavin as indicated. The position of DNA-GyraseB complex is indicated. Lane 1 (without protein) & lane 2 with (WTPfGyrB) are control reactions. (B) DNA supercoiling activity of PfGyrB (45 nM), *E. coli* GyrB (45 nM) and in combination with $GyrA_{Ecoli}$ (35 nM) in the presence or absence of Acriflavin as described in materials and methods. Lane 1 and lane 7 are only relaxed DNA without any protein. "OC", "L" and "S" indicate open circular, linear and supercoiled DNAs respectively. (C) Analysis of DNA dependent ATPase activity of PfGyrB with different concentrations of Acriflavin. ATPase reactions were carried out by NADH-coupled enzymatic assay. The reaction rates of PfGyrB with or without DNA were plotted against coumeramycin or different concentrations of Acriflavin as indicated.

SUMMARY OF THE INVENTION

Figure 1A:
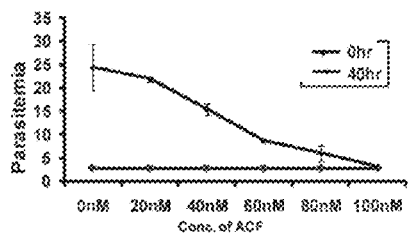
FIG. 1: Effect of Acriflavin on in vitro growth of 3D7 and W2 strains. Synchronized chloroquine susceptible 3D7 (A) and Chloroquine resistant W2 (B) parasites at ring stage (~16-20 hrs) were treated with 20 nM to 100 nM of Acriflavin and parasitemia were counted at different time points (post-treatment) as indicated. (C) In each case, parasitemia were determined at the end of the first life cycle and plotted against different concentrations of Acriflavin/Proflavin. Each point/column represents the parasitemia of the mean of triplicates with standard deviations. (D) Stage specific effect of Acriflavin in in-vitro culture of 3D7 strains: Acriflavin was treated in Ring (12-24 hrs), Troph (24-36 hrs) and Schizont stage (36-48) parasites and followed up to next life cycle (60 hrs). Parasite growth inhibition was assessed by microscopy of giemsa stained smear at different time points as indicated.

The present invention relates to determining anti-plasmodial activity of Acriflavin and discloses Acriflavin as an antimalarial agent.

One of the embodiments of the present invention provide a method of screening anti-plasmodial activity of Acriflavin wherein said method comprises assessing growth inhibition of *plasmodium* in vitro in chloroquine susceptible and chloroquine resistant *plasmodium* by Acriflavin; or measuring in-vivo *plasmodium* killing ability of Acriflavin; assessing localization of Acriflavin at different stages; and analyzing effect of Acriflavin on gyrase activity wherein said method utilizes Acriflavin in nano-molar range.

In another embodiment the method of screening anti-plasmodial activity of Acriflavin, comprises of determining the mechanism of Acriflavin inhibition of *plasmodium* growth in vitro and in vivo, by inhibiting the DNA binding activity of PfGyrB and DNA dependent ATP hydrolysis activity of Gyrase B in *plasmodium falciparum* species and from which it can also be deduced that when Acriflavin is administered at a nano-molar range 70 to 90% reduction in drug resistant parasites is obtained.

Yet another embodiment of the present invention provides a screening method for determining stage specific effect of Acriflavin in progression of *Plasmodium* growth in vitro, effect of Acriflavin inhibition of *plasmodium* in vivo, localization of Acriflavin in live malaria parasite, and the effect on DNA metabolic enzymes.

Still another embodiment of the present invention provide a screening method of determining anti-*plasmodium* activity of Acriflavin which results in deducing that the active component of Acriflavin is Trypflavin.

Another embodiment of the present invention provide a screening method, wherein when Acriflavin is administered in range of 20 to 100 nano-molar inhibits the growth of drug resistant *plasmodium* parasites by targeting the DNA binding activity of PfGyrB and DNA dependent ATP hydrolysis activity of Gyrase B in *Plasmodium falciparum* species.

Yet another embodiment of the present invention provides a test method that determines the target for antibacterial activity of Acriflavin is DNA topoisomerase or bacterial gyrase.

Still another embodiment of the present invention provide a screening method, wherein gyrase is a type II topoisomerase with two subunits (A and B) capable of supercoiling reaction comprising relieving positive supercoiling and introducing negative supercoiling which is preferred state of bacterial circular chromosome.

In another embodiment the inhibition of DNA binding activity of PfGyrB by Acriflavin starts at a concentration above 20 µM and the supercoiling reaction is affected at 1 µM.

A further embodiment of the present invention provide a screening method, wherein it is determined that when Acriflavin is administered it effected all three intra-erythrocytic stages of *Plasmodium falciparum*, namely, the ring stage, trophozoite stage and the multinucleated schizont stage and the more affected being the trophozoite stage parasites.

Still another embodiment of the present invention provides a screening method, wherein it determines that Acriflavin starts inhibiting the DNA binding property of PfGyraseB at a concentration of >20 μM and the supercoiling reaction mediated through PfGyrB-PfGyrA complex is affected at 1 μM wherein supercoiling reaction of Gyrase is dependent on the ATP hydrolysis activity of Gyrase B.

Yet another embodiment of the present invention provide a screening method, wherein it is determined that Acriflavin on administration is distributed in parasite cytoplasm in early stages and gets specifically accumulated in the parasite nucleus in the later stages.

Another embodiment of the present invention provides a screening method, wherein from the test method it was determined that Acriflavin accumulates in the infected RBC found in parasitophorous vacuole, but is not accumulated in uninfected RBC.

Still another embodiment of the present invention provides a screening method, wherein it was determined that nano-molar range for normal strain lies between 40 to 60 nano-molar and for chloroquine resistant W2 parasites it is in the range of 60 to 80 nano-molar.

A further embodiment of the present invention provides a screening method, wherein from the difference in activity of Proflavin and Acriflavin at different drug concentrations the active component of Acriflavin is deduced to be Trypflavin.

Another embodiment of the present invention provides a screening method wherein the potent uptake and retention of Acriflavin is effected by the efficient uptake and retention of Acriflavin by the parasites.

Yet another embodiment of the present invention provides a method, wherein it is determined by the test method that Acriflavin had potent antimalarial activity both in vitro and in vivo at a nano-molar range.

Still another embodiment of the present invention provides a screening method, wherein it is determined that Acriflavin have multiple targets which lower the possibility of rapid incidence of drug resistance.

Another embodiment of the present invention provide an anti-malarial agent comprising Acriflavin wherein Acriflavin is a mixture of 3,6-diamino-10-methylacridnium chloride (trypaflavin) and 3,6-diaminoacridine (proflavin) wherein when administered at a nanomolar range inhibit the DNA binding activity of PfGyrB and DNA dependent ATP hydrolysis activity of Gyrase B in *Plasmodium falciparum* species thereby preventing the drug resistant activity of the parasites and thereby making it a potent anti-malarial agent.

Still another embodiment of the present invention provides a composition comprising Acriflavin as an effective anti-malarial drug wherein Acriflavin is present in a nano-molar range.

Yet another embodiment of the present invention provides use of Acriflavin in the preparation of an anti-malarial medicament wherein Acriflavin is present in the range of 20 nano-molar to 100 nano-molar wherein Acriflavin inhibits *Plasmodium* growth in vitro and in vivo and wherein *Plasmodium* is *Plasmodium falciparum*.

DETAILED DESCRIPTION OF THE INVENTION

The present invention shows that Acriflavin has an antimalarial activity in both in vitro and in vivo working in the nanomolar range. Moreover, Acriflavin is accumulated specifically in the infected RBC containing parasites and not in the uninfected RBC. Gyrase is a potential target of Acriflavin in vitro.

Acriflavin is a mixture of 3,6-diamino-10-methylacridinium chloride (Trypflavin) and 3,6-diaminoacridine (Proflavin). To determine the antimalarial activity of Acriflavin in vitro, synchronised ring stage, Chloroquine sensitive (3D7) and Chloroquine resistant (W2) *P. falciparum* (~2.5% parasitemia) parasites were incubated with a range of Acriflavin concentrations. After the Acriflavin treatment, the parasitemia was calculated in each case. Further, the anti-malarial property of Acriflavin vs Proflavin was also evaluated. The results indicate that Proflavin is ineffective against malaria parasite in vitro.

Intra-erythrocytic stages of *P. falciparum* include the ring stage following invasion, the replicating trophozoite stage and the multinucleated schizont stage before the rupture of the red blood cell producing new parasites ready for the invasion. To address the issue that whether Acriflavin arrests the parasite growth in a stage specific manner, synchronised asexual stage parasites were treated with Acriflavin at ring, trophozoite and schizont stage followed by incubation of the parasites in the presence of Acriflavin till the next life cycle. It was found that Acriflavin affected the growth of the parasites in all the stages.

The anti-parasite activity of Acriflavin in the in vitro culture motivated to study the anti-malarial activity of Acriflavin in mouse model infected with *Plasmodium berghei*. This is further described hereinafter as Example 3. The results of the study clearly indicate that Acriflavin is also a potent antimalarial in vivo.

The anti-malarial activity of Acriflavin both in vitro parasite culture and in vivo animal model raises some important issues related to its uptake and accumulation in the parasites. For this purpose, mixed stage parasites were exposed to Acriflavin and subsequently observed under fluorescence microscope. Acriflavin was not found in the uninfected RBC. Moreover, within the infected RBC, it was found only within the parasitophorous vacuole.

It has been shown that acrB mutation in *E. coli* GyrB makes it sensitive to Acriflavin that may result due to the reduced affinity of *E. coli* gyrase to DNA. Interestingly, *Plasmodium* has both the subunits homologous to *E. coli* Gyrase A and B, essential for apicoplast DNA replication. Moreover, one residue equivalent to acrB mutation present in *E. coli* Gyrase B is also present in Pf gyrase B. The present invention also investigates out whether Acriflavin will affect PfGyrase activity.

Gyrase is a two subunit (A and B) enzyme, where the A subunit (GyrA) is responsible for cleavage and re-ligation reaction and is targeted by quinolones class of drugs (Ciprofloxacin). The B subunit (GyrB) is an ATPase and is targeted by coumarins (Coumeramycin A1, novobiocin). This enzyme may be involved in the replication and maintenance of the 35 kb apicoplast DNA circle [Raghu Ram E V et al., 2007; 154 (1):30-9].

First, the DNA binding activity of PfGyraseB was examined in presence of Acriflavin in gel shift assay. It was found that Acriflavin starts inhibiting the DNA binding property of PfGyraseB at a concentration >20 μM. The effect of Acriflavin on the supercoiling reaction mediated by gyrase was also examined The supercoiling reaction of Gyrase is dependent on the ATP hydrolysis activity of Gyrase B. It has been shown that PfGyrB is targeted to the apicoplast where it binds apicoplast DNA in vivo and in vitro it binds to AT-rich DNA leading to the stimulation of its ATPase activity [Dar A et al, Eukaryot Cell. 2009, 8 (11), 1759-69]. Further, the effect of Acriflavin was investigated on the DNA-dependent ATPase activity of Gyrase B.

The disclosure provided herein is representative and is not intended to restrict the scope of the present invention in any way. It must be understood that variations and modifications are possible based on the disclosure above without departing from the spirit and scope of the invention. As such, the present invention encompasses such variations and modifications.

The present invention is illustrated and supported by the following examples. These are merely representative examples and optimization details and are not intended to restrict the scope of the present invention in any way.

EXAMPLE 1

Acriflavin Inhibits the *Plasmodium* Growth In Vitro

Figure 1B:
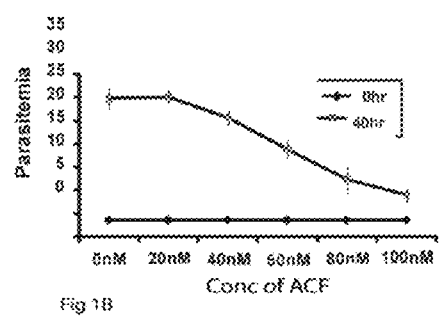
Figure 1C:
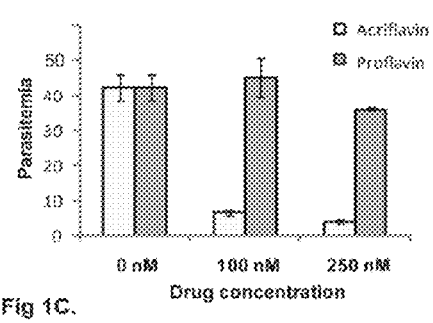

To determine the antimalarial activity of Acriflavin in vitro, synchronised ring stage, Chloroquine sensitive (3D7) and Chloroquine resistant (W2) *P. falciparum* (~2.5% parasitemia) parasites were incubated with a range of Acriflavin concentrations (0-100 nM). After 40 hours of the Acriflavin treatment, the parasitemia was calculated in each case. There was a considerable decrease in parasitemia with >90% inhibition of 3D7 parasites at 100 nM Acriflavin concentration as shown in FIG. 1A. Similarly, the growth of Chloroquine resistant parasites (W2) was reduced considerably (>70%) at 100 nM Acriflavin (FIG. 1B). The $IC_{50}$ value of Acriflavin lies in between 40 nM to 60 nM for the normal 3D7 strain where as 60-80 nM for Chloroquine resistant W2 parasites. Further, it was evaluated the anti-malarial property of Acriflavin vs Proflavin at 100 nM and 250 nM drug concentrations. The results indicate that Proflavin is ineffective against malaria parasite in vitro suggesting that Trypflavin is the active component in Acriflavin (FIG. 1C).

EXAMPLE 2

Figure 1D:
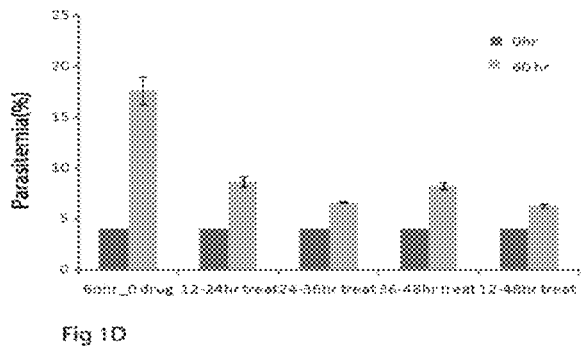

Stage Specific Effect of Acriflavin in Progression of *Plasmodium* Growth In Vitro To address the issue that whether Acriflavin arrests the parasite growth in a stage specific manner, synchronised asexual stage parasites were treated with 80 nM and 100 nM Acriflavin at ring (18-20 hours post invasion), trophozoite (28-30 hours) and schizont stage (38-40 hours) followed by incubation of the parasites in the presence of Acriflavin till the next life cycle. It was found that Acriflavin affected the growth of the parasites in all the stages. However the trophozoite stage parasites were affected mostly compared to ring and schizont stage parasites (FIG. 1D).

EXAMPLE 3

Acriflavin Inhibits the *Plasmodium* Growth In Vivo

Figure 2A:
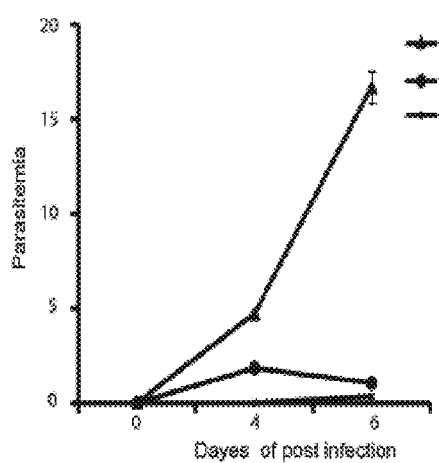
FIG. 2: In vivo measurement of parasite killing ability of Acriflavin. (A) Graph shows average percentage of parasitemia and days of post infection of untreated, chloroquine treated and Acriflavin treated, *P. berghei* infected mice. (B) Demonstrates rate of viability of chloroquine and Acriflavin treated vs untreated mice plotted against time.
Figure 2B:
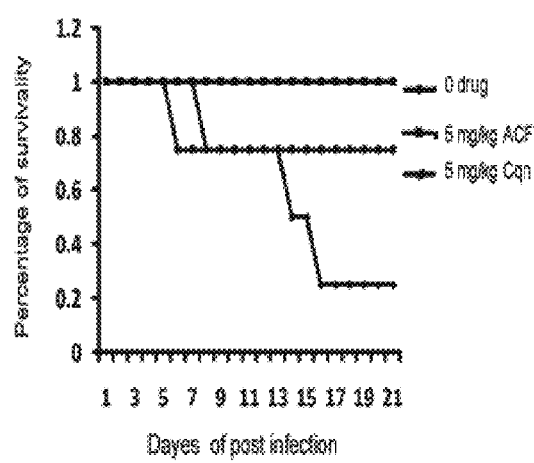

The mice were divided into three groups (each group had 4 mice). For four consecutive days, group I was injected subcutaneously with 5 mg Acriflavin/kg body weight; group II received 5 mg Chloroquine/kg body weight and the group III received no drug and served as control in this experiment. Every alternate day the parasitemia from the tail blood was calculated. The untreated control mice developed 16% parasitemia at the end of day 6, where as parasitemia in Acriflavin and Chloroquine treated mice was calculated as 1% and 0.33% respectively as indicated in FIG. 2A. The mouse groups were kept under observation for 3 weeks after the drug treatment. The survivability rate of the Acriflavin treated mice group was 100% and that of Chloroquine treated mice was 75% where as only 25% survivability rate was observed in untreated control mice (FIG. 2B). No drug-related effects on body weight or general condition of animals were noticed over the dosing and recovery periods. These results clearly indicate that Acriflavin is also a potent anti-malarial in vivo.

EXAMPLE 4

Localization of Acriflavin in Live Malaria Parasite

Figure 3:
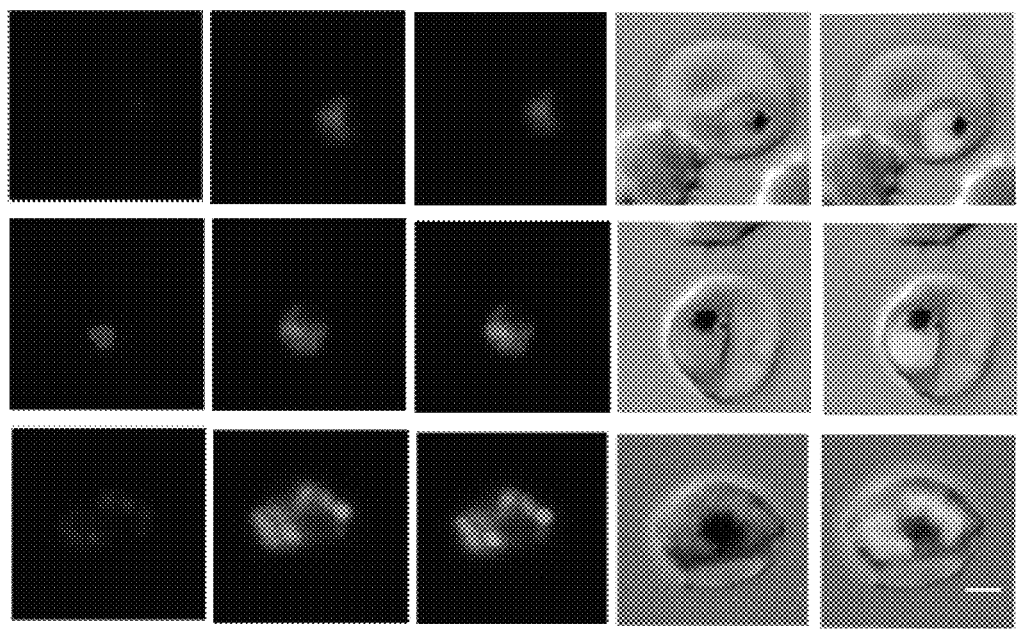
FIG. 3: Fluorescence microscopy of localized Acriflavin in different stages of *P. falciparum*. Fluorescence of Acriflavin was determined in live *P. falciparum* parasites by using excitation spectra @ 488 nm. Figureure shows intrinsic fluorescence of Acriflavin superimposed on DAPI representing nucleus of *P. falciparum*. All the fluorescence was finally superimposed on the bright field images. The results indicate that Acriflavin is present only in the infected RBC and not in the uninfected RBC.

To investigate the uptake and accumulation of Acriflavin in the parasites mixed stage parasites were exposed to 100 nM Acriflavin for three hours and subsequently observed under fluorescence microscope. DAPI was used for nuclear staining, and 488 nm excitation was used to view Acriflavin accumulation. Merge panels of Acriflavin and DAPI clearly indicate that although Acriflavin is distributed in parasite cytoplasm in early stages but gets specifically accumulated in the parasite nucleus in the later stages (FIG. 3). Interestingly, Acriflavin was not found in the uninfected RBC. Moreover, within the infected RBC, it was found only within the parasitophorous vacuole. The specific accumulation of Acriflavin in the parasites may have detrimental effect on parasite metabolic processes.

EXAMPLE 5

The Effect of Acriflavin on DNA Metabolic Enzymes

The DNA binding activity of PfGyraseB was examined in presence of Acriflavin (0-100 µM) in gel shift assay. It was found that Acriflavin starts inhibiting the DNA binding property of PfGyraseB at a concentration >20 µM. The effect of Acriflavin on the supercoiling reaction mediated by gyrase was also investigated. It was found that the DNA supercoiling activity mediated through EcGyrA-EcGyrB complex is not affected up to 4 µM Acriflavin concentration whereas supercoiling reaction mediated through PfGyrB-EcGyrA complex is affected even at 1 µM Acriflavin concentration (FIG. 4B).

The supercoiling reaction of Gyrase is dependent on the ATP hydrolysis activity of Gyrase B. It has been shown earlier that PfGyrB is targeted to the apicoplast where it binds apicoplast DNA in vivo and in vitro it binds to AT-rich DNA leading to the stimulation of its ATPase activity [Dar A et al, Eukaryot Cell. 2009, 8 (11), 1759-69; Dar A et al., Eukaryot Cell. 2007; 6 (3):398-412.]. Further, the effect of Acriflavin was investigated on the DNA-dependent ATPase activity of Gyrase B. It is found that the ATP hydrolysis activity of Gyrase B is stimulated several folds in the presence of DNA, However, Acriflavin inhibited the stimulation of ATP hydrolysis activity in a concentration dependent manner (FIG. 4C).

Overall, these results show that the supercoiling reaction which requires the DNA binding activity of PfGyrB and DNA dependent ATP hydrolysis activity of Gyrase B are inhibited in the presence of Acriflavin.

We claim:
1. A method of screening anti-Plasmodial activity of Acriflavin, wherein said method comprises:
   (a) assessing growth inhibition of *Plasmodium*, in vitro, in chloroquine susceptible and cloroquine resistant *Plasmodium* by Acriflavin; or measuring, in-vivo, *Plasmodium* killing ability of Acriflavin;

wherein said method utilizes Acriflavin in a nano-molar range and wherein said growth inhibition of *Plasmodium* is by inhibition of DNA binding activity of PfGyrB and DNA dependent ATP hydrolysis activity of Gyrase B in *Plasmodium* and wherein Gyrase B is a type II topoisomerase capable of supercoiling reaction comprising relieving positive supercoiling and introducing negative supercoiling of circular genomes during DNA replication in bacteria and apicoplast of *Plasmodium*.

2. The method as claimed in claim 1 wherein said inhibition of DNA binding activity of PfGyrB by Acriflavin starts at a concentration above 20,000 nM.

3. The method as claimed in claim 2 wherein said supercoiling reaction is affected at 1,000 nM.

4. The method as claimed in claim 1 wherein 70 to 90% reduction in drug resistant parasites is obtained.

5. The method as claimed in claim 1 wherein said *Plasmodium* is *Plasmodium falciparum*.

6. The method as claimed in claim 1 wherein Acriflavin is present in the range of 20 nM to 100 nM.

7. The method as claimed in claim 6 wherein Acriflavin is present in the range of 40 nM to 60 nM for chloroquine susceptible parasites and is present in the range of 60 to 80 nM for chloroquine resistant W2 parasites.

8. The method as claimed in claim 1, wherein Acriflavin affects the trophozoite stage of *Plasmodium falciparum*.

9. The method as claimed in claim 1, wherein Acriflavin accumulates in the *Plasmodium falciparum*-infected RBCs.

10. The method as claimed in claim $1_1$ wherein the active component of Acriflavin is Trypaflavin.

11. An anti-malarial agent comprising Acriflavin wherein Acriflavin is a combination of 3,6-diamino-10-methylacridnium chloride (Trypaflavin) and 3,6-diaminoacridine (Proflavin), wherein Trypaflavin is the active component and when administered at a nano-molar range inhibits the DNA binding activity of PfGyrB and DNA dependent ATP hydrolysis activity of Gyrase B in *Plasmodium falciparum*, and wherein Acriflavin affects the ring stage, the trophozoite stage and the multinucleated schizont stage of *Plasmodium falciparum*, thereby making it a potent anti-malarial agent.

12. A method for the preparation of an anti-malarial medicament comprising: adding Acriflavin into the medicament, wherein Acriflavin is present in the range of 20 nM to 100 nM and wherein Acriflavin affects the ring stage, the trophozoite stage and the multinucleated schizont stage of *Plasmodium falciparum*.

13. The anti-malarial agent as claimed in claim 11 wherein Acriflavin inhibits *Plasmodium* growth in vitro and in vivo.

14. The method of claim 1, wherein Acriflavin affects the ring stage, the trophozoite stage, and the multinucleated schizont stage of *Plasmodium falciparum*.

\* \* \* \* \*